(12) United States Patent
Madry et al.

(10) Patent No.: US 8,788,029 B2
(45) Date of Patent: Jul. 22, 2014

(54) HEART ANALYSIS METHOD AND APPARATUS

(75) Inventors: Andrew Madry, Cherrybrook (AU); Stuart Philip Thomas, Cheltenham (AU)

(73) Assignee: Cuoretech Pty Ltd., Cherrybrook NSW (AU)

( * ) Notice: Subject to any disclaimer, the term of this patent is extended or adjusted under 35 U.S.C. 154(b) by 1914 days.

(21) Appl. No.: 11/664,621

(22) PCT Filed: Oct. 5, 2005

(86) PCT No.: PCT/AU2005/001526
§ 371 (c)(1),
(2), (4) Date: Nov. 16, 2007

(87) PCT Pub. No.: WO2006/037172
PCT Pub. Date: Apr. 13, 2006

(65) Prior Publication Data
US 2008/0194979 A1    Aug. 14, 2008

(30) Foreign Application Priority Data
Oct. 5, 2004    (AU) .................................. 2004905706

(51) Int. Cl.
*A61B 5/04*    (2006.01)

(52) U.S. Cl.
CPC ........................................ *A61B 5/04* (2013.01)
USPC ........................................................... 600/523

(58) Field of Classification Search
CPC .......... A61B 5/00; A61B 5/0002; A61B 5/02; A61B 5/04; A61B 5/05; A61B 5/07; A61B 5/0033; A61B 5/103; A61B 5/0402
See application file for complete search history.

(56) References Cited

U.S. PATENT DOCUMENTS

| | | | |
|---|---|---|---|
| 5,391,199 A | 2/1995 | Ben-Haim | |
| 6,216,027 B1 | 4/2001 | Willis et al. | |
| 6,839,588 B1 * | 1/2005 | Rudy | 600/523 |
| 7,187,964 B2 * | 3/2007 | Khoury | 600/509 |

FOREIGN PATENT DOCUMENTS

| | | |
|---|---|---|
| EP | 1070480 A2 | 1/2001 |
| WO | W09724981 | 7/1997 |

* cited by examiner

*Primary Examiner* — Christopher D Koharski
*Assistant Examiner* — Elizabeth K So
(74) *Attorney, Agent, or Firm* — Howard & Howard Attorneys PLLC

(57) ABSTRACT

A method and device for monitoring heart behavior. In particular, a visual aid for clinician in which regions of the heart having aberrant characteristics can be displayed. A number of electrodes are positioned near/on an endocardium; electrical signals from the electrodes are monitored and recorded. A variability of a time varying parameter is calculated from each electrode location and displayed on a cardiac image. A user can select the parameter and measurement properties of the parameter, wherein the variability of the parameter is displayed and aberrant behavior can be detected.

34 Claims, 5 Drawing Sheets

HEART ANALYSIS METHOD AND APPARATUS

The invention relates to a method and apparatus for monitoring heart behaviour. In particular, the invention monitors a number of cardiac performance parameters, such as local activation variability, to characterise heart behaviour (function). The invention assists a clinician to visualise cardiac regions displaying aberrant characteristics.

BACKGROUND TO THE INVENTION

The heart can be thought of as an electro-biomechanical pump. Electrical signals stimulate muscles to contract in a controlled manner to achieve complex pumping actions. It is known that aberrant conduction of electrical activity in the heart can lead to arrhythmias that may cause morbidity and/or death.

Drugs have been developed to treat these conditions but they have low efficacy in many cases and dangerous potential side-effects. An alternate technique is radio-frequency ablation of the sites in the myocardium (heart muscle) believed to be responsible for the initiation or maintenance of arrhythmias.

During normal heart operation there are multiple electrical signals that travel through the myocardium triggering a muscle response. It can occur that an anatomical region changes its conductive properties (perhaps due to injury) thus causing the electrical signals to be diverted or blocked. In some cases an anatomical obstacle or functional alteration in myocardial electrical properties can cause the electrical impulse to degenerate into wavelets that circulate and suppress the normal activation signal. Changes in conductive properties may cause a signal to arrive sooner, or later at a site remote from the source of the abnormal circulating activity. In either case the normal sequence of activation of contraction of heart tissue is disrupted.

Radio-frequency ablation seeks to treat the arrhythmia by ablating the source of aberrant signals or interrupting circulating electrical activities at a critical pathway. To do this it is essential that the critical pathway or abnormal signal source be accurately located. This is done using endocardial mapping techniques.

The most basic form of mapping of the electrical activity in the heart is done by moving a catheter with electrodes within the chamber of the heart and observing the resultant electrical signals (electrograms). The clinician compares a recording made at one position with recordings made at other positions. Example parameters extracted are: the relative timing of electrical activations or the shape (morphology) of the electrical signal. Abnormal behaviour can be localised in this way.

The measurement of relative time delay across the endocardial surface is facilitated by using more than one catheter device. For example if one catheter is kept in a fixed position and another is moved around, then the clinician can determine the relative electrical timing relationships from one location with respect to another.

An extension of this approach is to use catheters with multiple electrodes. This allows electrograms at several positions to be measured at the same time.

A further extension to this is called global mapping of the heart chamber activity. Electrograms are recorded simultaneously over the whole chamber using the appropriate multi-channel device. A fundamental limitation here is the size of device that may be inserted into a vein to encapsulate the wires required for connection to each electrode. With global mapping the timing relationships between various locations can be viewed simultaneously. To some extent this takes a mental load off the clinician who is required to remember the various timing relationships.

Medical device technology has emerged in the last few years making possible the capture of signals from many electrodes simultaneously. An example is a device such as the so called basket catheter. This appears to have been first described in U.S. Pat. No. 5,156,151 titled "Endocardial Mapping and Ablation System and Catheter Probe", assigned to Cardiac Pathways Corporation, and related patents.

A limitation with this sort of mapping device is that the electrodes are generally spaced too far apart to resolve fine spatial detail. Another problem is maintaining contact of the electrodes with the heart chamber wall. The number of electrodes is limited by the diameter of catheter that can be safely inserted. Individual wires are required to connect to each electrode. There are typically 64 electrodes.

The concept of global mapping lends itself to the display of isochronal maps and velocity maps of the endocardial surface. An isochronal, or equal time map, is a graphical representation of locations on the endocardial surface where electrical activation times are the same. The lines or contours that join these locations of equal activation time represent wavefronts of electrical activation. The electrical wavefront can be thought to travel in a direction perpendicular to these contour lines. Contour lines are generally shown at equal increments in time or alternatively colour is used to indicate equal time increments. When contour lines are spaced close together this indicates a lower velocity (ie it takes a wavefront longer to travel a certain distance). This graphical representation using a contour map can be referenced to the anatomical location of the measurement positions. Maps can be represented in a 2D or 3D fashion.

The velocity of wavefront propagation can be computed from the measured time delay between known electrode locations. In a similar fashion to the isochronal map a graphical display can be used to represent the variation of this parameter on the endocardial surface.

These mapping concepts have been used by researchers for many years.

Such a system is described in U.S. Pat. No. 5,487,391, titled "Systems and Methods for deriving and displaying the propagation velocities of electrical events in the heart", assigned to EP Technologies. In this patent the activation time is measured at locations of an array of spaced apart electrodes (eg a basket). An algorithm is described to compute the spatial gradient of the electrogram activation time. This inverse of the magnitude of this value is taken as the velocity of propagation. A colour display is described to represent different velocity magnitudes at their relative spatial locations. The patent also refers to the display of the magnitude of other physiological parameters measured by an array of spaced apart sensors. The invention basically provides a snapshot and does not allow parameters to be observed over time.

EP Technologies describe a related system in their U.S. Pat. No. 5,494,042, titled "Systems and Methods for deriving electrical characteristics of cardiac tissue for output in iso-characteristic displays". This patent describes means for deriving an electrical characteristic of tissue lying in multiple paths between spaced apart electrodes. The electrical characteristic in this particular case is the tissue impedance. The patent also describes means for creating an output displaying in three dimensions, groups of equal electrical characteristics in spatial relation to location of the electrodes on the structure. Parameter values are assigned to an interpolated mesh. Colours are assigned to these values.

It is clear that useful information is obtained by the appropriate graphical display of physiological parameters spatially referenced to the endocardial surface of the heart.

Another technique for global mapping is a non-contact mapping technique. This is implemented in a commercial system known as Ensite by Endocardial Solutions Inc. This system is originally described in two patents assigned to Endocardial Therapeutics Inc: "Endocardial Mapping System" (U.S. Pat. No. 5,297,549) and "Heart Mapping Catheter" (U.S. Pat. No. 5,311,866).

U.S. Pat. No. 5,297,549 describes the limitations of traditional direct contact electrodes. These include spatial averaging effects due to the area of the electrode. The patent also describes the limitations of electrical potential map creation as a result of interpolation based on a "limited set of measurements". The Ensite system takes measurements made from a high resolution electrode array catheter device located inside the heart chamber, not in contact with the wall, and using mathematical extrapolation techniques, produces maps of the electrical potential at the endocardial chamber wall. The method relies on locating the endocardial surface accurately. An improvement to the location method is described in: "Endocardial Measurement Method" (U.S. Pat. No. 5,553,611). This uses an additional pair of excitation electrodes to generate an electric field inside the heart. Distance to the heart wall is derived from impedance measurements.

While in theory a high spatial resolution can be obtained, in practice the accuracy of the extrapolation of the electrical field is limited.

An advantage of the Ensite method (as described in the summary of the patent) is that an activation map can be created from a single heart beat once the geometry has been created. The maps created can be followed over time. This is unlike the roving catheter technique. Global mapping has an advantage over sequential mapping when there are unstable patterns of activation occurring ie activation patterns that may change significantly from beat to beat. This change may only be in a particular spatial region. The roving catheter technique relies on the spatial activation pattern remaining the same within the time of the roving process.

However even with the availability of multi-channel mapping devices clinicians in practice still rely on manually manipulating a flexible catheter around the heart chamber to localize electrical activity to very specific regions.

To enhance this approach methods have been devised to spatially locate the roving electrode within the heart chamber in 3D. Acoustic means, magnetic field means and electric field means have been used for this purpose. A map is built up by moving the roving electrode around keeping track of its location in 3D space and measuring the electrogram sensed at each location. Such a system is described in U.S. Pat. No. 5,391,199, assigned to Biosense Inc. This patent describes a 3D catheter position location system. The location system generates position signals in the catheter tip in response to externally applied magnetic fields, generated by electromagnetic field generator coils situated outside the body.

The method allows a 3D representation of activation timing to be generated. An advantage of this approach is that it obviates the need for continuous fluoroscopic imaging to locate catheters (which is not desirable because of X-ray exposure to patient and operators). The fluoroscopic imaging approach has limitations anyway because it provides only a 2D cross sectional view (a 3D perspective may be obtained by sequentially rotating this view).

A 3D graphical display may be built up by moving a single catheter around the heart chamber. This technique is used in the Carto System available from Biosense Inc.

Another possible method of catheter localisation is by using acoustic signal means. The Real Time Position Management System by Cardiac Pathways is such a system. This is described in U.S. Pat. No. 6,216,027, assigned to Cardiac Pathways Corporation. This system uses one or more ultrasound reference catheters to establish a fixed 3D coordinate system within a patient's heart using triangulation. The coordinate system is represented graphically in 3D on a video monitor.

Another 3D localisation method is called LocaLisa from Medtronic Inc. This system senses impedance changes between a catheter and reference points.

In the previous two methods reference electrodes are kept in fixed positions which are located in known regions and the position of the roving electrode is tracked relative to these fixed positions.

Despite the developments in electrode design and the improvement in signal measurement, the clinician still has a limited range of data from which to assess the correct location for tissue ablation. Additional tools for visualisation and assessment are required.

OBJECT OF THE INVENTION

It is an object of the present invention to provide a clinician with a dynamic display of the variability of time-varying cardiac parameters.

It is a further object of the present invention to provide a system able to display the variability of time-varying cardiac parameters.

Further objects will be evident from the following description.

DISCLOSURE OF THE INVENTION

In one form, although it need not be the only or indeed the broadest form, the invention resides in a method of identifying cardiac regions having aberrant conductive properties including steps of:
measuring a plurality of electrical signals from an endocardium;
recording positions of each electrical signal;
computing a variability of a time varying parameter from said electrical signals; and
displaying said variability at said positions on a cardiac image.

Suitably, the variability may represent change in a parameter between multiple locations or a parameter at a single location.

Variability is suitably displayed graphically using appropriate visual indicators.

The method may further include the step of recording a time sequence of variability at each position and displaying the time sequence on demand.

BRIEF DETAILS OF THE DRAWINGS

To assist in understanding the invention preferred embodiments will now be described with reference to the following figures in which.

DETAILED DESCRIPTION OF THE DRAWINGS

Figure 1:
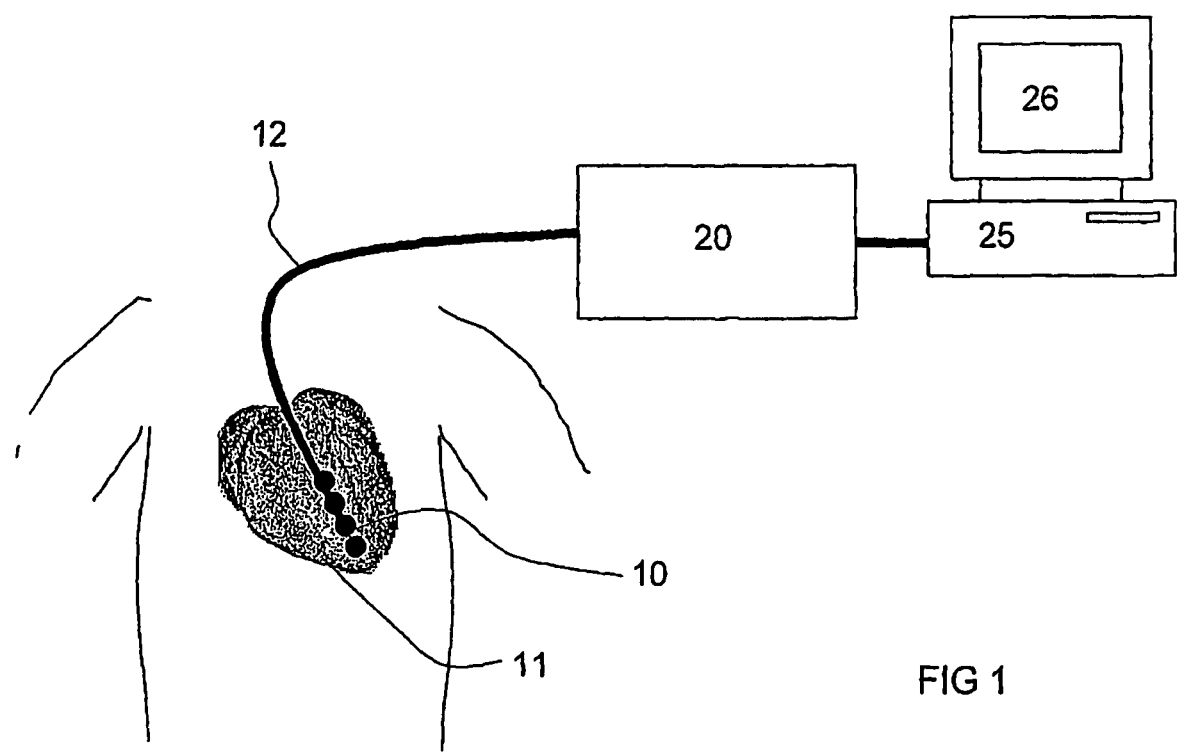
FIG. 1 shows schematically the application of the apparatus to a patient.

In describing different embodiments of the present invention common reference numerals are used to describe like features.

In FIG. 1 there is shown an apparatus comprising a bundle of electrodes 10 that are positioned within a heart 11 via a catheter 12, usually inserted along an artery or vein but possibly by direct puncture of a pericardium. Signals from the electrodes 10 are amplified, filtered and digitised by signal conditioner 20. The conditioned signals are analysed in computer 25 to extract significant parameters, such as activation frequency, variability of activation direction and variability of activation velocity, as discussed in detail below. The extracted parameters are displayed in various ways on screen 26.

The design of the bundle of electrodes 10 is selected for the particular parameter(s) being measured. For instance, a minimum of three electrodes is required to unambiguously measure local activation velocity. A typical electrode bundle consists of four electrodes arranged in a square around a central fifth electrode. Bundles of up to ten or more electrodes are known in the prior art.

Figure 2:
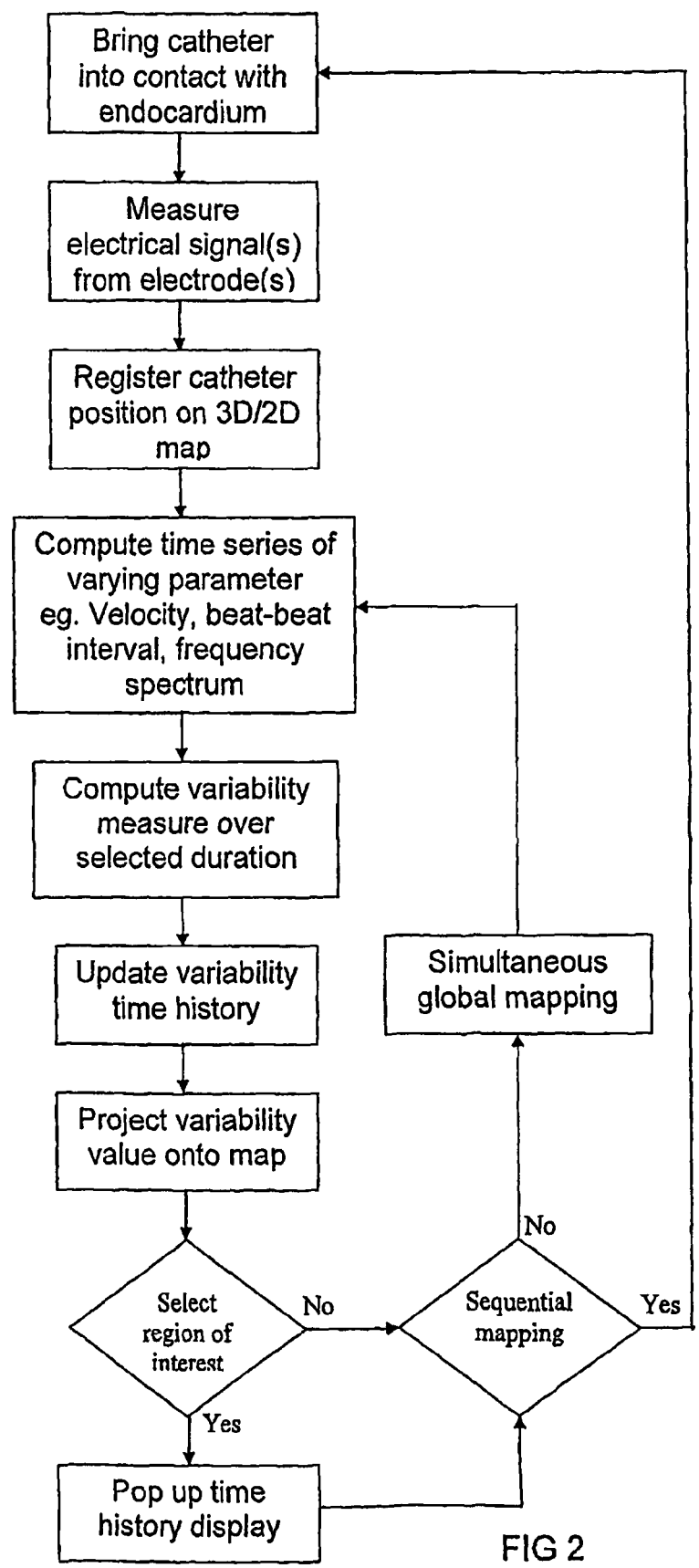
FIG. 2 shows a flow chart of one method of working the invention.

The steps involved in working the invention are shown in FIG. 2. The method is commenced by applying electrodes to the cardiac region. The clinician manipulates the catheter to position the electrodes in a location to be measured. The electrical signals from the electrode are recorded and digitised for analysis. The positions of the electrodes are registered on a two-dimensional or three-dimensional map of the heart, using known acoustic means, magnetic field means or electric field means.

A time sequence of measurements is recorded and used to calculate one or more parameters such as velocity, beat interval, frequency spectrum, etc. The calculation of parameters is described in greater detail below. From the time sequence of parameters the variability over a selected duration is calculated. The variability is displayed to the clinician as a useful indicator of function. By recording from multiple sites (simultaneously or sequentially) regional variations in these indicators can be established. This Information may be used to determine the source of abnormal electrical impulses or the position of critical pathways. This information is important for guidance of curative ablation procedures. This technique is described below in greater detail.

To assist the clinician to interpret the calculated variability, a display of variability is overlaid on a cardiac map. A number of different display formats are possible depending on the nature of the parameter and the preference of the user. Preferably, a user can select a parameter and measurement properties of the selected parameter.

Figure 3:
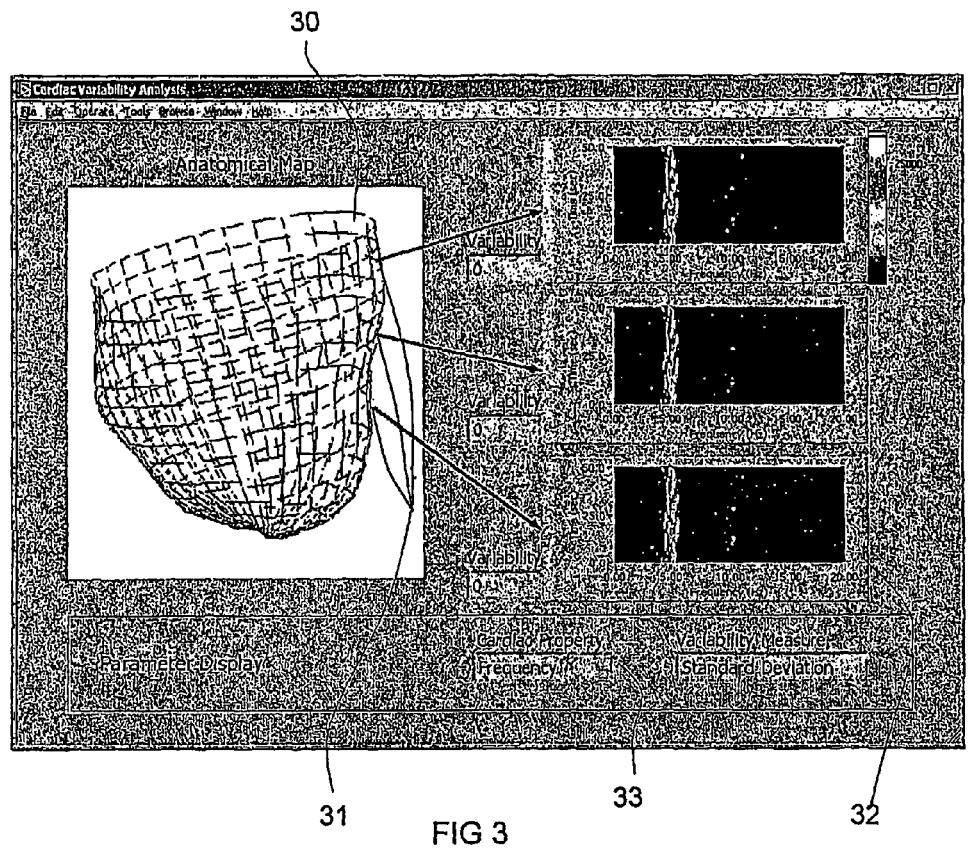
FIG. 3 shows a typical display generated by the invention.

Referring specifically to FIG. 3, a 3D or 2D image of a cardiac region is displayed as an anatomical map 30 on one part of a screen. The electrode positions 31 are displayed on the image. An image 32 displaying variability of a selected parameter is displayed on another part of the screen. In FIG. 3 the image 32 is a waterfall plot, as described below. The display and operating parameters are displayed at the bottom 33 of the screen.

The description applies to the situation where movable localised electrodes are used. If a global mapping electrode system is used it is possible to select any region of the cardiac image for display of variability graphs.

Figure 4:
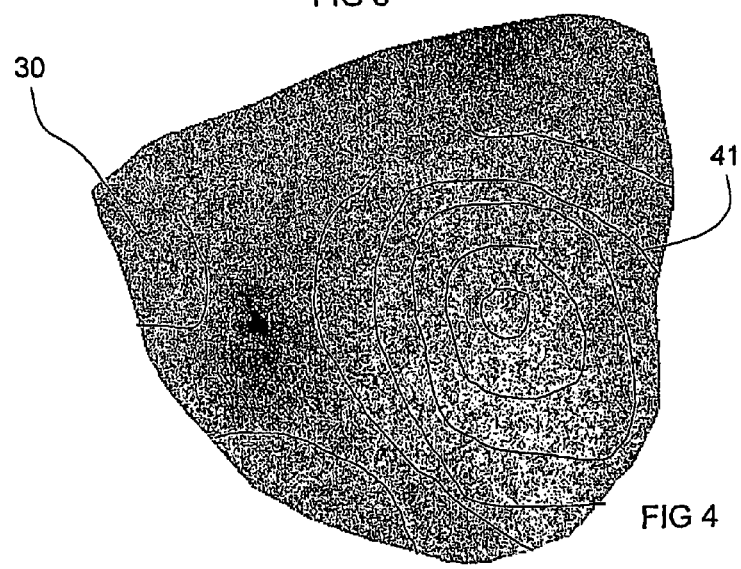
FIG. 4 shows a detailed view of a portion of the display of FIG. 3.

FIG. 4 displays an enlarged detailed view of the anatomical map 30. The map displays regions of similar properties joined by lines, such as 41. These lines are known as isochrones if they are linking areas of equal time. They may also link areas of equal velocity, equal activation amplitude, equal variability, etc. In addition, anatomical maps can indicate variability of a parameter at certain positions and display the variability in a multidimensional manner.

Although it is known to monitor specific properties of cardiac tissue (eg beat to beat interval, frequency, velocity) at distinct times and look for significant changes as a result of some intervention, it has not been suggested to continuously monitor the variability of a parameter over a surface and create spatial maps of this variability. In the known techniques the value of the parameter is generally taken as an instantaneous or a mean value estimated over some time period. The invention monitors the temporal variability of physiological properties over the endocardial surface. In addition, the parameters may be based on temporal measurements from a single spatial location (ie. Dominant Frequency), a spatial property (ie. wavefront velocity) or spatial coherence property where measurement locations are further apart. The system provides a function to track the variability of a parameter as a function of time.

Besides the utility of examining the spatial distribution of variability of parameters the method also allows tracking of changes to the short term variability of a parameter in localised regions that may occur as a result of some intervention such as pacing, ablation or administration of a pharmacological agent.

The system characterises the temporal properties of the physiological parameter by the variability. By variability, it is meant by how a parameter value changes in time. There are many ways that a sampled time series representing the continuous variation of the instantaneous value of a measured parameter can evolve. The invention is not limited to any particular variability measure.

In one approach, a plot of a particular parameter is constructed, such as shown in FIG. 3. This plot shows energy in the signal as a function of frequency and is displayed as a function of time. To facilitate the display of the relationship between the three quantities on a 2D display, energy can be displayed in colour. The x axis can represent frequency and the y axis time. This is commonly known as a waterfall plot. A Dominant Frequency in a signal is seen as a bright line travelling down the display. Alternatively time can be represented along the x axis and frequency the y axis.

This type of plot shows the frequency characteristics evolving over time and allows the user to visually estimate the variance of a spectral result. It also allows the user to observe subtle changes in the frequency patterns.

If the appropriate electrode arrangement is used then multiple locations on the endocardial surface can be measured simultaneously. Alternatively a map can be built up sequentially as described previously.

Computer graphical techniques are used to display the measurement positions in the 3D display. At the measurement positions colour is used to indicate the value of the computed quantity. In the case of a frequency analysis this could be representative of the mean Dominant Frequency at that particular location. In this case the colour is used to represent a parameter computed over a predefined time period.

The user selects a particular region of the 3D or 2D display representing spatial measurement positions and then activates a popup graphical display of the time varying parameter of interest. Multiple popup displays may be provided to simultaneously view time varying parameters of interest. For example, in FIG. 3 there are multiple popup waterfall charts to display frequency variability at three different electrode positions. A unique feature of this system is that it allows the electrophysiologist to look for complex changes in the stability of electrical properties of one region with respect to another.

Particular abnormal physiological phenomenon or events (eg arrhythmia mechanisms) have characteristic patterns of variability. The spatial registration of variability provides useful clinical information. The manner in which the measured parameter dynamically changes at a particular location is also of clinical value and displayed by the system.

As well as visualizing the variability at a location there is clinical value in visualizing the difference in variability between locations. For example an area of tissue generating fibrillatory waves may be represented by a particularly stable pattern of interbeat interval. Regions further away may tend to be more variable as they are driven by a more organized spatially fixed activation source. Alternatively a region of scarred, damaged, or functionally abnormal tissue, may be represented by a higher degree of variability for a parameter such as the cardiac velocity direction. This comparison is also possible with the system, as is evident by a review of FIG. 3 and FIG. 6.

Furthermore, differences in short term estimates of variability and how they evolve over time can provide useful information to the electrophysiologist. This invention provides means of computing and displaying this data.

A key aspect of the invention is the calculation and display of the variability in a parameter at a location over time. The invention is not limited to any particular parameter or any particular definition of variability.

In particular, an embodiment of the invention allows a user to select a parameter and measurement properties of the selected parameter. Typical parameters that may be monitored include the activation time, which is the absolute time of activation of each beat. Comparison of activation times at different locations generates an isochronal map. This may be displayed by the invention along with the measures of variability in activation time at each location. This is known as the variability of the beat to beat interval Another useful parameter to monitor includes local velocity of the endocardium. A map of local velocity can be based on velocity measured at various spatial locations. Measurement can be recorded simultaneously at all locations using a global mapping system or sequentially using a roving catheter/electrode technique.

Since velocity is a vector quantity, the magnitude and direction of the velocity can be monitored. In one embodiment of the invention, the variability of the wavefront velocity and the wavefront direction over the endocardial surface can be monitored. Unstable tissue regions can be located since the velocity magnitudes and the wavefront directions vary considerably when compared to stable tissue regions.

Various methods are known for determining variability. These include: standard deviation; degree of entropy; degree of chaos; and a correlation dimension. All of these techniques are known in the literature and may be applied in the invention.

Another useful measure is the degree of variability as a function of time, ie how the variability changes in time. This can be obtained by segmenting time records and computing the required parameter over sequential time blocks. One embodiment of the invention uses variability indicators that may be extracted from measured signals over shorter time durations.

Another measure implemented in the invention is a calculation of nonlinear parameters such as, correlation dimension, based on the sampled intracardiac electrical signal rather than on the beat to beat interval series as is commonly done in Heart Rate Variability (HRV) analysis on surface ECG signals. The length of the time record required is therefore much smaller and lends itself to tracking variations of the parameter as a function of time.

Another useful 3D graphical technique which can be utilised to display multi-dimensional data includes on a glyph. An example of a glyph includes using rendered spheres located at each spatial measurement position on a 3D graphical display. Multiple properties of the rendered sphere such as the colour, radius, and surface roughness can be used to represent multidimensional data. This allows properties such as mean Dominant Frequency (ie. colour) and variance (ie. radius) to be displayed simultaneously. Alternatively, the glyph could be an arrow whose length indicates a wavefront speed and direction of the arrow indicating the wavefront direction.

Generally, graphical persistence can be incorporated into the glyph technique. For example, a wavefront speed (ie length of arrow) is continuously monitored and displayed, such that the previous speed gradually fades and eventually disappears while the latest speed displayed brightest. An exponential weighting may be applied to the persistence level, thereby providing a clinician with a visual indication of the variability of the parameter monitored. Hence, when the wavefront speed (ie. Length of arrow) is stable; the display would provide a sharp image. Conversely, if the wavefront speed varied considerably, the display would provide a fuzzy image, or unfocussed image. Although an example of graphical persistence has been illustrated using the glyph technique, a person skilled in the art would easily appreciate that graphical persistence can be incorporated into many display techniques such as power spectrum plots and 3D anatomical surface maps.

It should be noted that the invention implements measures, such as the correlation dimension, which will be known to persons familiar with HRV analysis of surface ECG data. However, the invention utilizes measures from intracardiac electrograms which indicate local electrical activity, rather that the overall properties of the heart that are determined from surface ECG.

Apart from activation time, the frequency content of the cardiac electrical signal also provides useful information. This may be computed using known Fourier Transform methods. The Fourier Transform of a series of regular sharp activations exhibits a large number of harmonics. Frequency analysis has particular application when activation is of a fibrillatory nature. There tends to then be a Dominant Frequency peak.

In this invention a Short Time Fourier Transform or other time frequency analysis method is used to process the local signal at each location on the endocardial spatial map. The fundamental frequency of the local activation signal is extracted. The Dominant Frequency is tracked as a function of time and the variability of this frequency is calculated. The variability may be defined by any of the means described above.

Alternatively, Joint Time Frequency Analysis (JTFA) methods can also be used. It has been found that overlapping blocks by up to 90% is a useful technique in tracking changes in frequency content. With visual display methods like the waterfall plot, the operator can carry out an assessment of stability of a Dominant Frequency, or the presence of changing spectral content.

Figure 5:
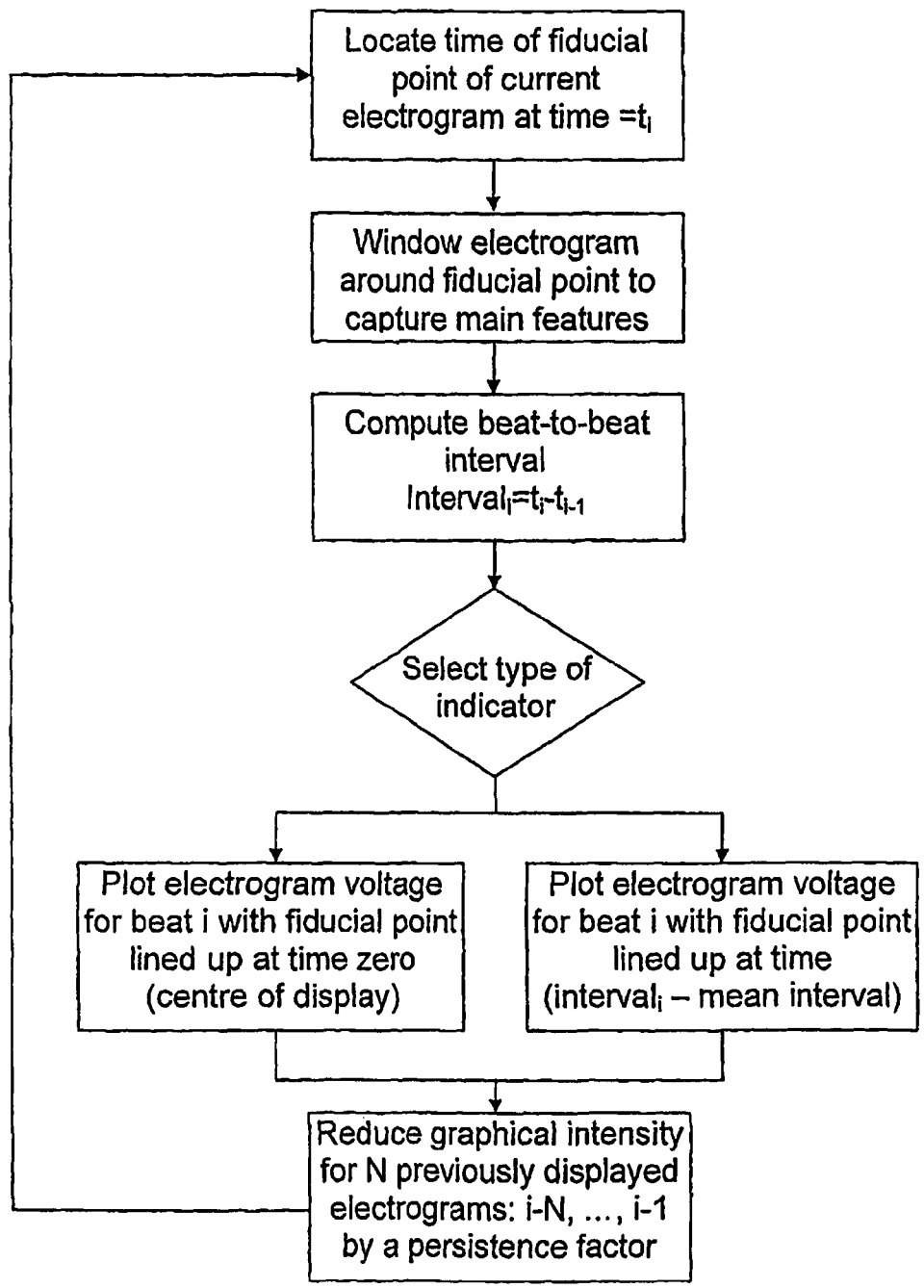
FIG. 5 shows a flow chart of the steps of calculating a visual indicator.
Figure 6:
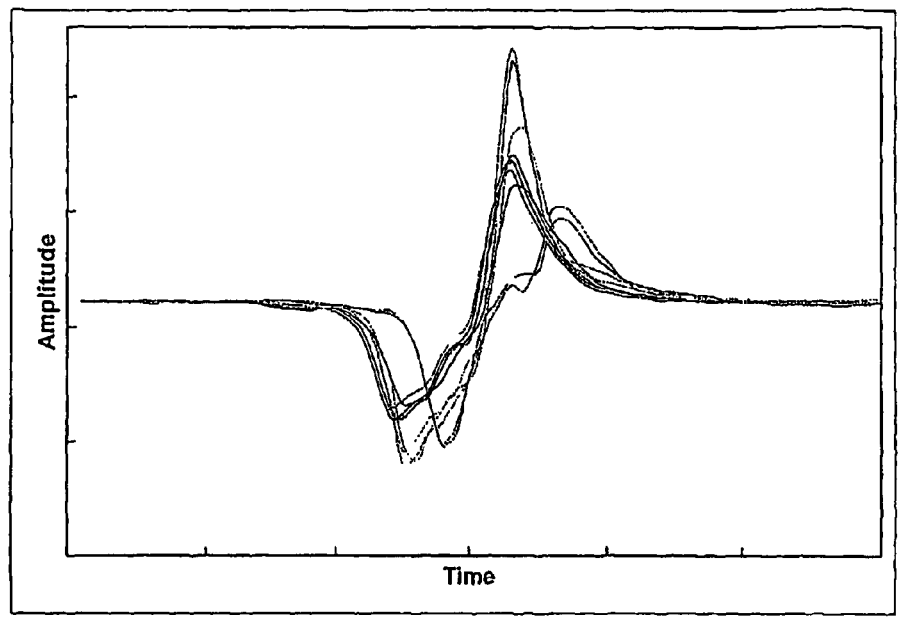
FIG. 6 shows a visual indicator.

FIG. 5 shows a flow diagram for the sequence of steps used to create a visual indicator that may be used to indicate the variability of the cardiac electrogram. In this example two parameters of the cardiac electrogram are visualized. One is the morphology, or the shape, that varies from beat to beat and the other is the beat to beat Interval. The system measures the currently received electrogram and calculates a fiducial point. There are several well known means for identifying the fiducial point. An example is the time of maximum negative slope of the electrogram. The electrogram is windowed to contain the main features of the beat. Successive electrograms are displayed on top of each other on a graphical display, such as shown in FIG. 6. Graphical persistence can be used to fade out past electrograms. The position of display on the time axis of this display depends on the type of indicator required. In one case the fiducial times are lined up at the centre of the display. If all electrograms were identical it would appear as if there was only one trace. In practice there is a variation in electrogram from beat to beat and this type of display highlights this variability.

Figure 7:
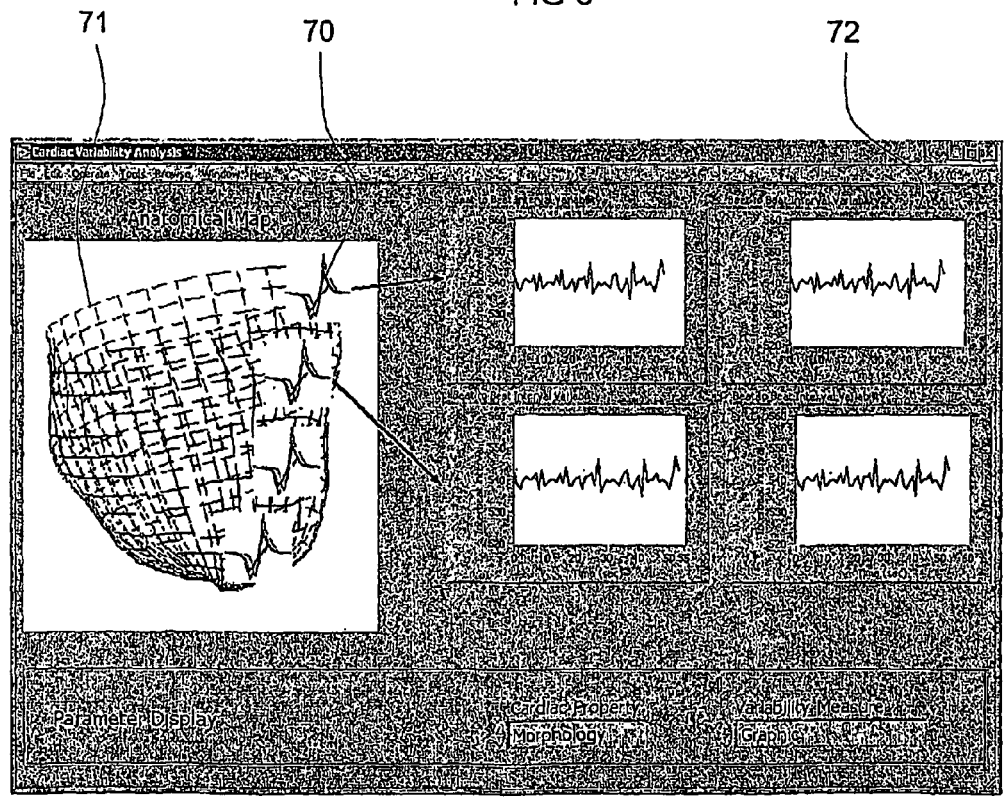
FIG. 7 shows an alternate display incorporating the visual indicator of FIG. 6.

Looking particularly at FIG. 7, an example of a particular display form is shown. A visual indicator 70 is displayed at each electrode location on a cardiac image 71. Each visual indicator 70 displays beat to beat variability at the indicated location. Separate graphs show the beat to beat interval 72 at each location.

An alternative method is to display the successive electrogram beats offset from the central zero position of the graph by an amount equal to the difference of the current beat to beat interval with a running mean interval computed over a specified time period. In this way the variation of beat to beat interval can be visualized. For example if beat to beat interval is getting progressively less the electrograms will appear to shift to the left of the zero position until the beat to beat interval is constant again. If the variation is random the display will appear equally weighted with electrograms on either side of zero position. A visual persistence factor, adjustable by the operator, is used to visually weight the current electrograms more than previous electrograms. Electrograms from a designated time previously will be no longer visible.

These are just some examples of indicators that may be used to highlight variability dynamically in conjunction with a spatial map of anatomy. It will be appreciated that the example of FIGS. 3 and 7 are indicative of the type of display that is generated by the invention, and other display formats are envisaged.

In regards to the forementioned description, the method and system can include a standard microprocessor operatively connected to a computer readable medium such as a random access memory (e.g., static random access memory (SRAM)), read only memory (e.g., programmable read only memory (PROM) or electrically erasable programmable read only memory (EPROM)), or hybrid memory (e.g., FLASH memory) as is well known in the art. The medium then comprises computer readable program code components that, when processed by the microprocessor, are configured to execute the above described steps of the method and system as described in FIGS. 2 and 5.

Throughout the specification the aim has been to describe the invention without limiting the invention to any particular combination of alternate features.

The invention claimed is:

1. A method of identifying cardiac regions having aberrant conductive properties including steps of:

measuring a plurality of electrical signals from an endocardium wherein the measuring includes a time sequence;

recording positions of each electrical signal;

calculating a time varying parameter from the measured time sequence of electrical signals;

computing a time-series variability of the time varying parameter over a selected duration from said electrical signals to thereby monitor the temporal variability of the time varying parameter which represents the continuous variation of an instantaneous value of the time varying parameter; and displaying said time-series variability at said positions on a cardiac image.

2. The method of identifying cardiac regions having aberrant conductive properties of claim 1 further including a step of allowing a user to select said parameter and select a graphical representation for said time-series variability.

3. The method of identifying cardiac regions having aberrant conductive properties of claim 2 further including a step of displaying changes in said time-series variability by displaying changes in said graphical representation of said time-series variability.

4. The method of identifying cardiac regions having aberrant conductive properties of claim 1 further including a step of recording variability for each said position and displaying said time-series variability for each position in real time.

5. The method of identifying cardiac regions having aberrant conductive properties of claim 1 further including a step of recording a time sequence of variability for each said position and displaying said time sequence in real time.

6. The method of identifying cardiac regions having aberrant conductive properties of claim 1 further including a step of displaying said cardiac image using an anatomical map and said time-series variability using a waterfall plot.

7. The method of identifying cardiac regions having aberrant conductive properties of claim 1 further including a step of allowing a user to select a region on said cardiac image and activating at least one popup display, displaying said time-series variability of selected region.

8. The method of identifying cardiac regions having aberrant conductive properties of claim 1 further including a step of displaying said time-series variability of a cardiac electrogram.

9. The method of identifying cardiac regions having aberrant conductive properties of claim 8 further including a step of receiving electrogram signals from said electrodes and computing a fiducial point.

10. The method of identifying cardiac regions having aberrant conductive properties of claim 1 further including a step of allowing a user to select said parameter and select a measurement property of said parameter.

11. The method of identifying cardiac regions having aberrant conductive properties of claim 1 further including a step of computing time-series variability of a wavefront velocity and wavefront direction.

12. The method of identifying cardiac regions having aberrant conductive properties of claim 1 further including a step of allowing a user to select a visual persistence factor of said time-series variability.

13. The method of identifying cardiac regions having aberrant conductive properties of claim 1 wherein the time series variability is selected from the group consisting of a standard deviation, degree of entropy, degree of chaos and a correlation dimension.

14. A system of identifying cardiac regions having aberrant conductive properties including:

a plurality of electrodes measuring electrical signals from an endocardium wherein the measuring includes a time sequence;

a recording device recording a position for each electrical signal;

a calculating device calculating a time varying parameter from the measured time sequence of electrical signals;

a computing device calculating a time-series variability of a time varying parameter over a selected duration from said electrical signals to thereby monitor the temporal variability of the time varying parameter which represents the continuous variation of an instantaneous value of the time varying parameter; and a display device displaying said time-series variability at said position on a cardiac image.

15. The system of identifying cardiac regions having aberrant conductive properties of claim 14, wherein said display device allows a user to select said parameter and select a graphical representation for said time-series variability.

16. The system of identifying cardiac regions having aberrant conductive properties of claim 14, wherein said display device displays changes in said time-series variability by displaying changes in said graphical representation of said time-series variability.

17. The system of identifying cardiac regions having aberrant conductive properties of claim 14, wherein said recording device records a time sequence of variability for each said position and displays said time sequence in real time on said display device.

18. The system of identifying cardiac regions having aberrant conductive properties of claim 14, wherein said display device displays said cardiac image using an anatomical map and the time-series variability using a waterfall plot.

19. The system of identifying cardiac regions having aberrant conductive properties of claim 13, wherein said display device allows a user to select a region on said cardiac image and activates a popup display of said time-series variability of selected region.

20. The system of identifying cardiac regions having aberrant conductive properties of claim 14, wherein said display device displays said time-series variability at said position over said cardiac image.

21. The system of identifying cardiac regions having aberrant conductive properties of claim 14, wherein said display device displays said time-series variability of a cardiac electrogram.

22. The system of identifying cardiac regions having aberrant conductive properties of claim 14, wherein said electrodes measure the electrogram signals from said endocardium and said computing device calculating a fiducial point.

23. The system of identifying cardiac regions having aberrant conductive properties of claim 14, wherein said display device allows a user to select said parameter and select a measurement property of said parameter.

24. The system of identifying cardiac regions having aberrant conductive properties of claim 14, wherein said computing device calculates time-series variability of a wavefront velocity and wavefront direction.

25. The system of identifying cardiac regions having aberrant conductive properties of claim 14, wherein said display device allowing a user to select a visual persistence factor of said time-series variability.

26. The system of identifying cardiac regions having aberrant conductive properties of claim 14 wherein the time series variability is selected from the group consisting of a standard deviation, degree of entropy, degree of chaos and a correlation dimension.

27. A computer program having a computer readable medium having a computer program logic recorded thereon for identifying cardiac regions having aberrant conductive properties, said computer program product comprising:

means for measuring a plurality of electrical signals from an endocardium wherein the measuring includes a time sequence;

means for recording positions of each electrical signal;

means for calculating a time varying parameter from the measured time sequence of electrical signals;

means for calculating a time-series variability of a time varying parameter over a selected duration from said electrical signals to thereby monitor the temporal variability of the time varying parameter which represents the continuous variation of an instantaneous value of the time varying parameter;

means for displaying said time-series variability at said positions on a cardiac image.

28. A computer program having a computer readable medium having a computer program logic recorded thereon for identifying cardiac regions having aberrant conductive properties, said computer program product as recited in claim 27 further comprising means for allowing a user to select said parameter and select a graphical representation for said time-series variability.

29. A computer program having a computer readable medium having a computer program logic recorded thereon for identifying cardiac regions having aberrant conductive properties, said computer program product as recited in claim 27 further comprising means for displaying changes in said time-series variability by displaying changes in said graphical representation of said time-series variability.

30. A computer program having a computer readable medium having a computer program logic recorded thereon for identifying cardiac regions having aberrant conductive properties, said computer program product as recited in claim 27 further comprising means for allowing a user to select said time series variability from the group consisting of a standard deviation, degree of entropy, degree of chaos and a correlation dimension.

31. A cardiac monitor comprising:

a plurality of electrodes arranged over an endocardial surface;

a signal receiver adapted to detect a time-series of electrical signals from said electrodes;

a detection device tracking positions of each said electrode of the plurality of electrodes;

a calculating device calculating a time varying parameter from the measured time sequence of electrical signals;

a computer device calculating a time-series variability of a time varying parameter over a selected duration from said electrical signals to thereby monitor the temporal variability of the time varying parameter which represents the continuous variation of an instantaneous value of the time varying parameter; and a visual device displaying said time-series variability at said positions on a cardiac image.

32. The cardiac monitor as recited in claim 31 wherein said computer device allows a user to select said parameter and select an indicia for said time-series variability.

33. The cardiac monitor as recited in claim 32 wherein said visual device displays changes in said time-series variability by displaying changes in said indicia.

34. The cardiac monitor as recited in claim 31 wherein the time series variability is selected from the group consisting of a standard deviation, degree of entropy, degree of chaos and a correlation dimension.

* * * * *

UNITED STATES PATENT AND TRADEMARK OFFICE
CERTIFICATE OF CORRECTION

Page 1 of 1

PATENT NO. : 8,788,029 B2
APPLICATION NO. : 11/664621
DATED : July 22, 2014
INVENTOR(S) : Andrew Madry and Stuart Philip Thomas It is certified that error appears in the above-identified patent and that said Letters Patent is hereby corrected as shown below:

In the Claims

Column 11, line 35, claim 19: delete "claim 13" and replace with -- claim 14 --.

Signed and Sealed this
Ninth Day of December, 2014

Michelle K. Lee
*Deputy Director of the United States Patent and Trademark Office*